United States Patent
Boute et al.

(10) Patent No.: US 7,082,334 B2
(45) Date of Patent: Jul. 25, 2006

(54) SYSTEM AND METHOD FOR TRANSMISSION OF MEDICAL AND LIKE DATA FROM A PATIENT TO A DEDICATED INTERNET WEBSITE

(75) Inventors: Wim Boute, Dieren (NL); Jos Van Hove, Schiedam (NL)

(73) Assignee: Medtronic, Inc., Minneapolis, MN (US)

( * ) Notice: Subject to any disclaimer, the term of this patent is extended or adjusted under 35 U.S.C. 154(b) by 599 days.

(21) Appl. No.: 10/020,880

(22) Filed: Dec. 19, 2001

(65) Prior Publication Data
US 2003/0114896 A1    Jun. 19, 2003

(51) Int. Cl.
*A61N 1/36* (2006.01)

(52) U.S. Cl. ....................................... 607/60

(58) Field of Classification Search ............. 607/30, 607/32, 60; 128/903, 904
See application file for complete search history.

(56) References Cited

U.S. PATENT DOCUMENTS

| | | | |
|---|---|---|---|
| 4,379,459 A | 4/1983 | Stein | |
| 4,476,868 A | 10/1984 | Thompson et al. | |
| 4,556,063 A | 12/1985 | Thompson et al. | |
| 4,821,723 A | 4/1989 | Baker et al. | |
| 5,131,388 A | 7/1992 | Pless | |
| 5,144,949 A | 9/1992 | Olson | |
| 5,158,078 A | 10/1992 | Bennet et al. | |
| 5,312,453 A | 5/1994 | Shelton | |
| 5,314,430 A | 5/1994 | Bardy | |
| 5,354,316 A | 10/1994 | Keimel | |
| 5,800,465 A | 9/1998 | Thompson et al. | |
| 5,843,138 A | 12/1998 | Evers et al. | |
| 6,418,346 B1 * | 7/2002 | Nelson et al. | 607/59 |
| 6,473,638 B1 * | 10/2002 | Ferek-Petric | 600/523 |
| 6,564,104 B1 * | 5/2003 | Nelson et al. | 607/60 |
| 6,738,671 B1 * | 5/2004 | Christophersom et al. | 607/60 |

* cited by examiner

*Primary Examiner*—Scott M. Getzow
(74) *Attorney, Agent, or Firm*—Daniel G. Chapik; Girma Wolde-Michael (57) ABSTRACT

The invention provides a system and method for easy and reliable connection of patient-originated medical data through a simple port of a computer to a dedicated web site. A device originating medical data, such as an implanted pacemaker, downloads data into a transmit/receive device, and the data is then transformed in an interface unit to be accepted by a simple port of a computer, e.g. a keyboard port or a mouse port. The patient logs on to a dedicated web site, and transfers the data along with typed input to the web site for analysis. Following analysis, a reply message is sent back to the patient, which may include a control instruction for modifying or reprogramming the operation of the device that is used to originate the medical data. For a pacemaker application, the data transformation is done at a simple interface unit that is portable and easily manipulated by the patient. For other applications such as monitoring data from a diabetic, the data is transformed by the interface unit, and may be stored daily in the PC and transmitted to the web site after collection of a predetermined number of days of data.

38 Claims, 8 Drawing Sheets

SYSTEM AND METHOD FOR TRANSMISSION OF MEDICAL AND LIKE DATA FROM A PATIENT TO A DEDICATED INTERNET WEBSITE

FIELD OF THE INVENTION

This invention relates to bi-directional communication systems and methods for transmission of medical data from an individual to a dedicated web site and, more particularly, for easy connection of patient medical data to a computer and then to a dedicated web site.

BACKGROUND OF THE INVENTION

One of the areas of medical device systems that has undergone great progress in the past decade is that of transmission of data. For example, implantable medical devices, such as cardiac pacemakers, incorporate the capacity to download data that has been sensed from patient cardiac signals through telemetry. Pacemaker and other implantable cardiac device systems have the capacity to collect and store a significant amount of data that is useful for control, and particularly for diagnostic purposes. This data is downloaded by telemetry to an external programmer, of the type disclosed in U.S. Pat. No. 5,843,138. As shown in the system of the aforementioned patent, such programmers also have the capability of transmitting control commands and new software routines for use by the pacemaker or other implanted device. Such programmers are in widespread use, but generally are quite sophisticated and are available for use only by a physician. As a consequence, they are usually only available in a medical facility.

In more recent years, emphasis has been placed on providing improved tele-monitoring of cardiac and other medical data, by connecting the pacemaker system or any other medical device that collects patient data, including the external programmer, with a more expanded communication system. Thus, it is known to acquire cardiac signals through transmission of signals by analog telemetry to a programmer type device, and then to subsequently convert the signals into data that can be connected through to the Internet. See Hutten et al, IEEE/EMBS, Oct. 30–Nov. 2, 1997, pages 974–976, disclosing a web browser based remote patient heart transplant monitoring system. However, such systems, and other currently proposed systems rely on a sophisticated interface device of a type not normally available to a patient, and in particular not when the patient is travelling. A further problem that limits easy transmission of patient data to the Internet is the need to record the data to a medium such as a floppy disc or CD, so that it is easily inputted into a computer. While such sophisticated equipment is available in a hospital or medical facility setting, it would rarely be available to a patient. This becomes even more so if the patient is traveling and away from the home environment. In such situations, access to a computer would be of little help if there were no easy means of getting medical data into the computer for subsequent passage across the Internet to a web site where it can be analyzed.

There is a great deal of work and investment presently being directed toward enhanced communication of medical and like data across the Internet for subsequent analysis. However, there remains a serious need for a system and method of enabling a patient, with minimum expense, to easily acquire medical data of various forms and transform it for input into a personal computer, so that the data can be transmitted to a dedicated web site wherever the patient can have access to a personal computer. Since personal computers are now widely available, the key is to provide a simple and relatively inexpensive manner of connecting the patient to the computer without the need of having a sophisticated programmer or equivalent interface device.

SUMMARY OF THE INVENTION

It is an object of this invention to provide a convenient way to connect a patient or the patient's device to a web site for transfer of patient medical and other data, in order to provide optimum mobility to the patient and yet provide security of interconnection from a personal computer to a dedicated web site. An object is thus the achievement of a system and method providing a patient with an easy and yet reliable method of communicating his or her personal cardiac data over the Internet to a web site where it can be evaluated, and to do so from any location where a personal computer can be located.

In view of the above objects, there is provided a system and method whereby a patient can download medical data from an implanted or external (e.g. blood pressure measurement equipment) medical device to a personal computer. The patient uses only a simple coupling device or equivalent for receiving patient signals, and a dedicated interface unit for transforming the medical data so that it can be inputted through a simple port of a personal computer. In particular, the system and method of this invention provide for inputting data through either a computer keyboard port or a mouse port of a personal computer, each of which is a simple port. Each of these ports is a simple bi-directional port, through which data can be inputted without the need for an intervening storage device such as a CD or a floppy disc. The system of the invention utilizes an interface unit designed to transform signal and other data into the form of digital data accepted by either a keyboard port or a mouse port.

In the practice of the invention, the overall scheme is for the patient to transmit across the Internet data that has been collected by an implanted pacemaker, an EKG machine, data from a blood glucose monitor, or other such medical device. The data stream may be originally all analog signals from a medical device, or the device data may be interspersed with digital signals originating with, for example, a keyboard. The patient logs on to a dedicated web site from his/her local computer, whereupon the local computer obtains patient application software, e.g. browser and (optional) plug in software modules, from the web site. The data source, either a simple programmer designed for collecting cardiac data, or other medical signal device, is connected through an interface unit to a selected simple port of the computer, e.g. the keyboard or mouse port. The medical data is downloaded from the patient device through the interface unit where it is transformed, and then inputted into the computer through the simple port. The data is then sent from the computer over the Internet to a dedicated host web site, e.g. a web site managed by an attending cardiologist or by a pacemaker manufacturer or through software with artificial intelligence. The host web site analyzes the patient data, and prepares and transmits a message and/or instructions back to the patient computer. The patient computer system displays the message, and, depending upon the received reply, can pass a control signal though the interface unit to the programmer to initiate reprogramming control of an implanted device.

In another exemplary embodiment, typically for a patient who obtains data on a regular basis, patient-specific application software is loaded into the patient's PC by conventional means. When the patient downloads data, e.g. daily, the computer application software analyzes the data, and stores data and/or results of the analysis, along with the date. The application software will determine when data should be downloaded to the web site, and prompt this to be done by the patient.

DESCRIPTION OF THE PREFERRED EMBODIEMENTS

Figure 1:
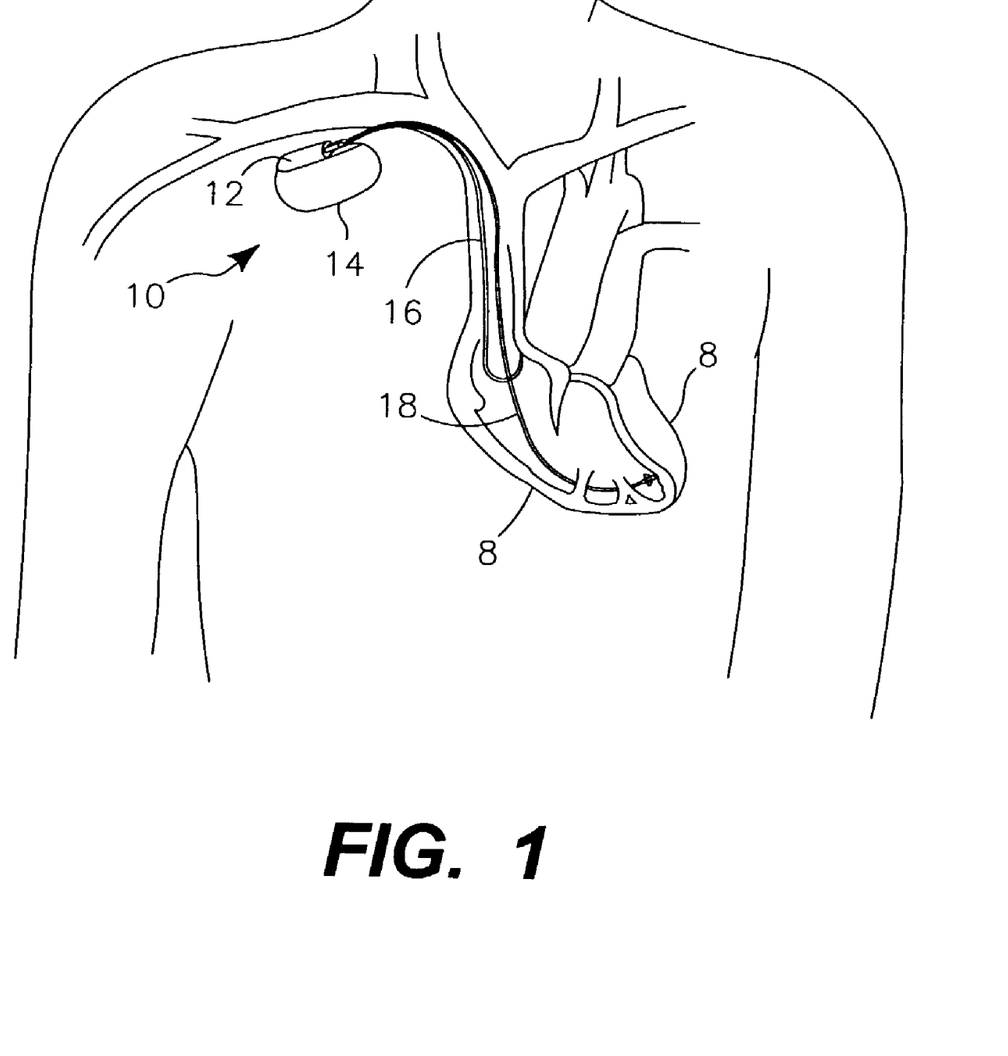
FIG. 1 is a simplified schematic view of one embodiment of an implantable medical device that can be employed in the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
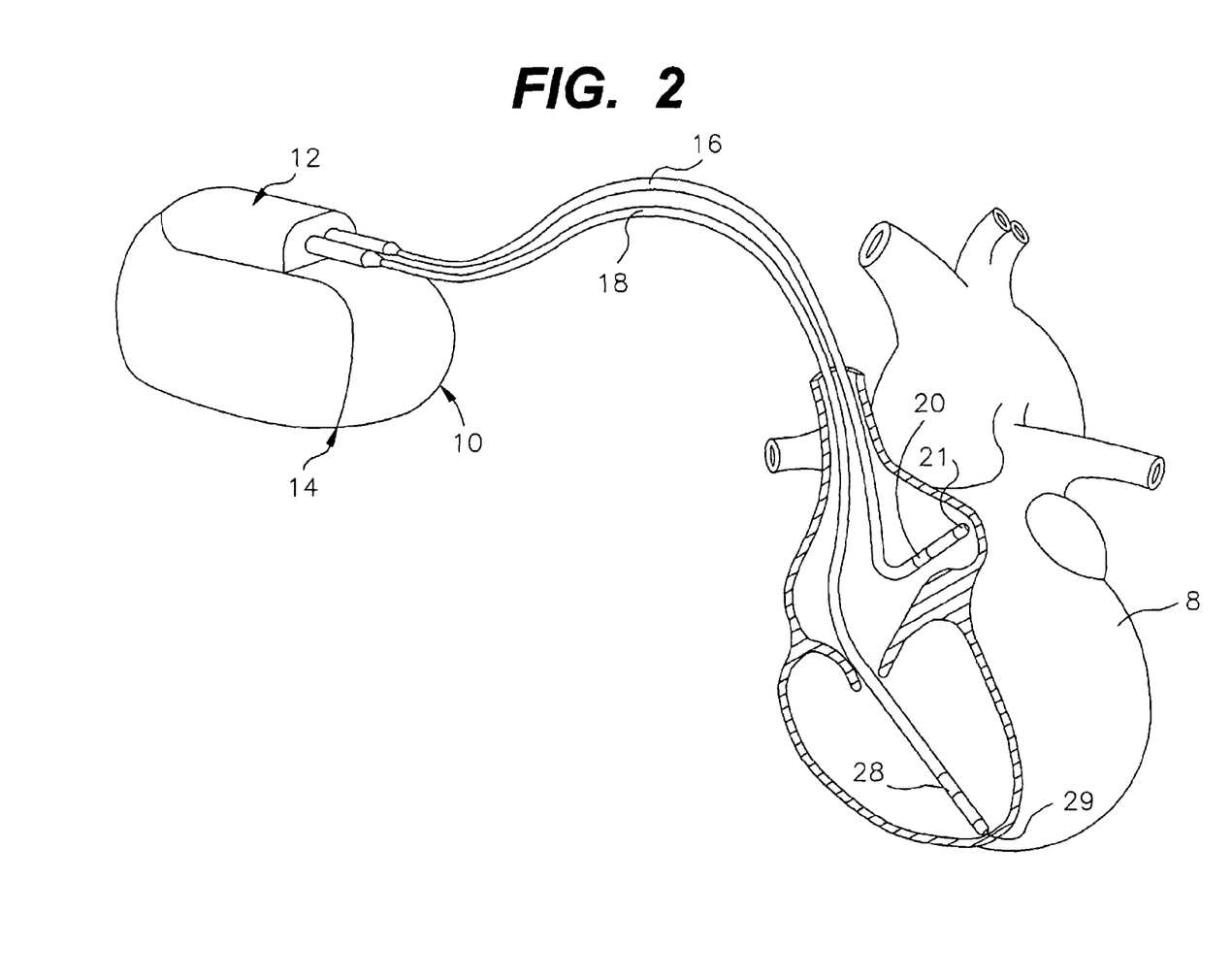
FIG. 2 is a graphic representation of an implantable medical device interconnected with a human or mammalian heart, illustrating the device connector portion and the leads between the device and the heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
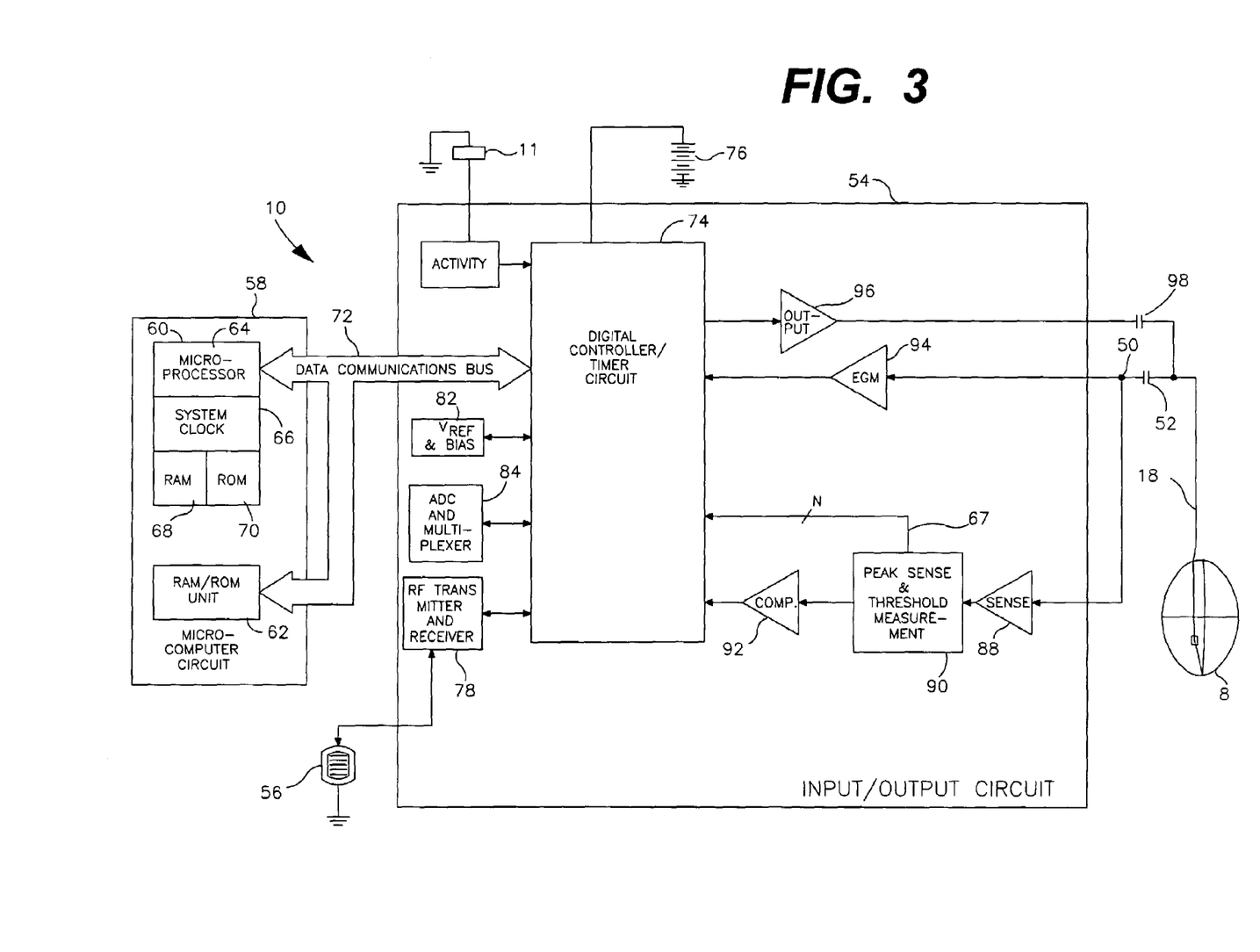
FIG. 3 is a functional schematic diagram showing the primary constituent components of an implantable medical device in accordance with an embodiment of this invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

Figure 9:
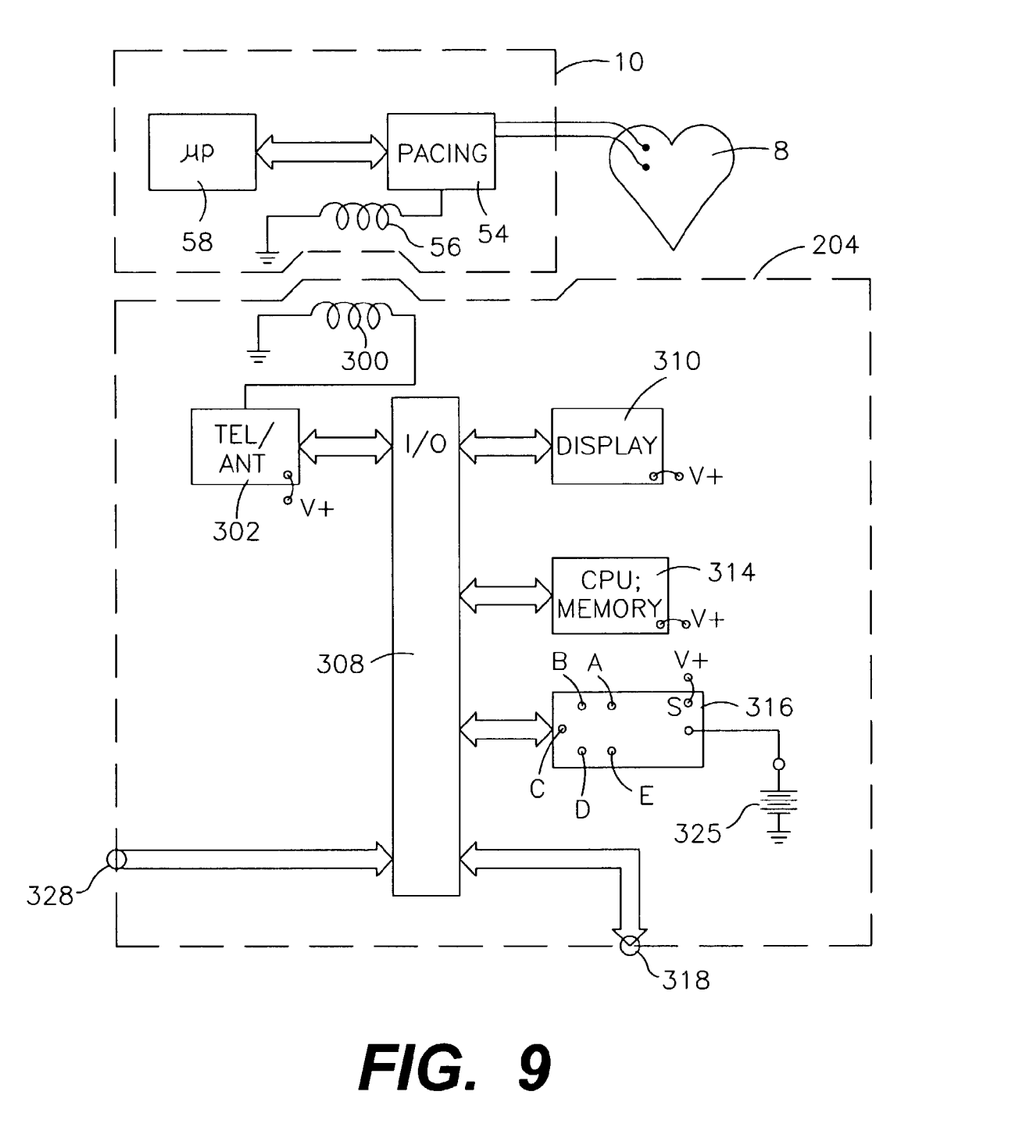
FIG. 9 is a block diagram of the primary components of a combined programmer-interface unit for use in the practice of this invention.

IMD 10 in FIG. 3 is most preferably programmable by means of an external programming unit (see FIG. 9). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker. See the discussion relating to FIG. 9, below, which illustrates a combined programmer and interface unit 204.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "realtime" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention. Implantable pacemakers currently have significant diagnostic capabilities, such as stored electrograms, data indicating heart rate trend, arrhythmia information such as onset mechanisms, premature beat counters, etc. This type of information is readily available in the device for transmission over the web.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's, such as hemodynqamic monitoring devices, implantable heart rate monitors and PCDs. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
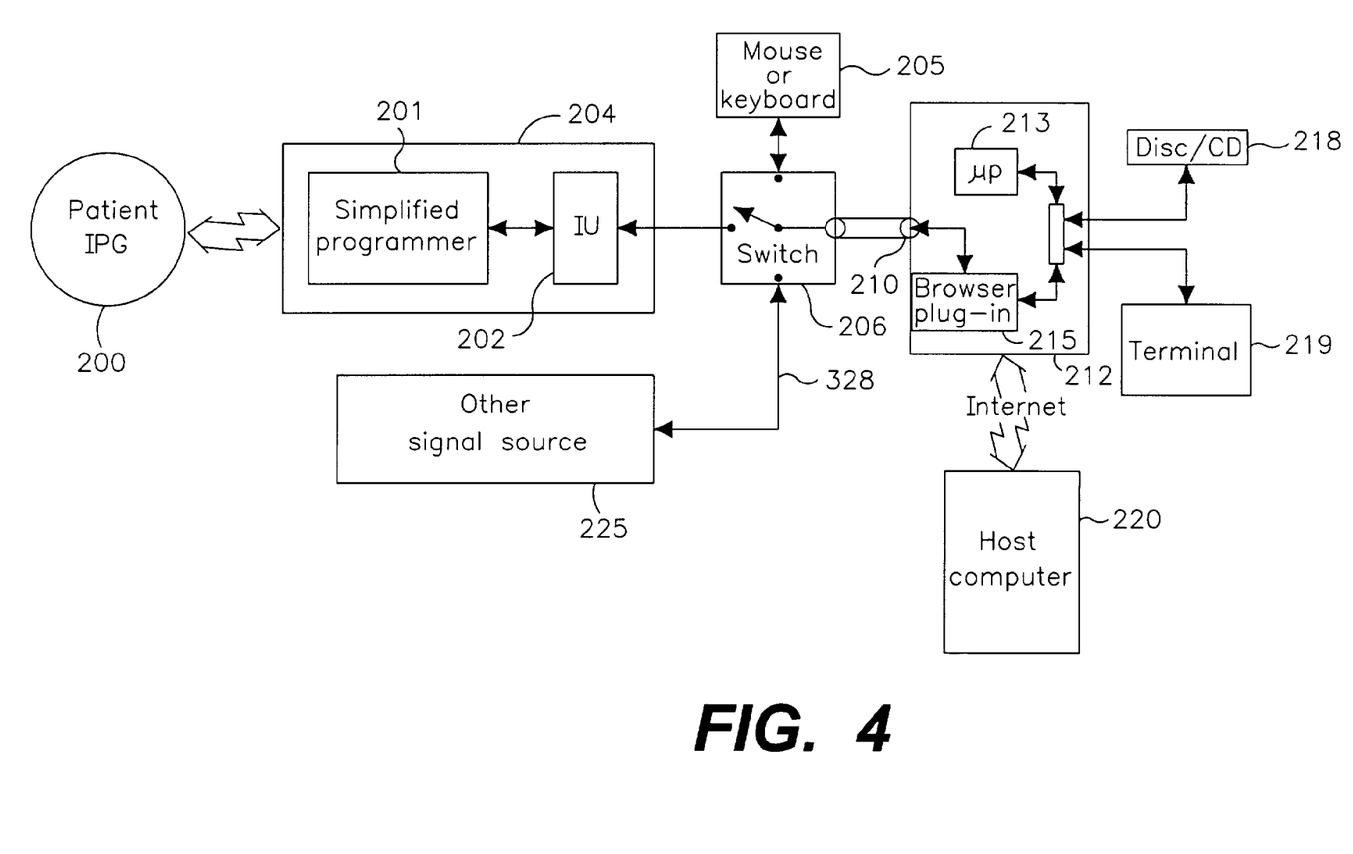
FIG. 4 is a schematic block diagram showing the primary components of a system for Internet transmission of data in accordance with this invention.

FIG. 4 is a block diagram illustrating the main components of a system in accordance with this invention. A patient IPG is shown at 200, and represents an implantable pacemaker or other implantable cardiac device. The IPG is able to store cardiac data, and download such data to a simplified programmer 201 having transmit/receive circuitry as is used in cardiac programmer devices. Unit 201 is a very simplified version of a programmer having a coil for picking up the telemetry signals from the IPG, a decoding and sampling circuit, and a connection for passing the sampled signals on to the interface unit (IU) shown at 202. The IU may be a separate device, or it may be housed with the simplified programmer in unit 204, as shown further in FIG. 9. Interface unit 202 preferably contains a microprocessor and performs the tasks of converting the analog signals from the medical device into digital signals, and then transforming the digital data so that it is in acceptable form for the port 210 of computer 212. The port 210 is, for this system, a simple port, defined as either the mouse port for receiving input from a mouse, or a keyboard port for receiving input from a keyboard. The simple port 210 is, for a typical PC type computer, a bi-directional port, meaning that it can receive data and also output data from the computer to another location.

In the practice of this invention, the transforming task of IU 202 can be done by hardware, although it is preferable to have software operation so that the transformation can be made for any simple type computer port that is available. In each case, the characteristics of the signals that are conventionally inputted to the simple port are utilized by the IU for transforming the data into an acceptable form. For a mouse port, the data must match the x-y data that is inputted by a mouse, as well as digital data representing clicks of the mouse, either left or right clicks. For an analog signal that contains x-y data, such as an electrocardiogram, the transformation is a simple transformation of each sampled digital value at each point on the curve into x-y data for receipt by the computer. If desired, the IU 202 may have buttons to simulate a click signal, which could indicate the start of a new graph that, e.g., could indicate the start of a new signal. For use with the keyboard input, each digital sample of a signal is transformed to a value that represents the input of a signal key or combination of keys, to represent a particular value. For transforming signal data, since samples are taken sequentially with time, each successive sample represents a time (Δt) later than the last sample so that y information is not necessary when transforming continuous signals. Thus, for either simple port that may be chosen, the transformation is easily accomplished by storing in the IU memory the characteristics of the mouse or keyboard, and using these characteristics as a lookup table for transforming the digital sample of the analog signal.

As seen in FIG. 4, a switch 206 is preferably interposed between the output of the IU 202 and the simple input port 210. The purpose of the switch is to enable the user to connect a cable from the input port (keyboard or mouse port) to the switch, which can be placed at a convenient position, e.g. near the computer. The mouse or keyboard then can be connected to one input of the switch, and the IU connected to the other. With this arrangement, under normal circumstances the patient can have the mouse or keyboard connected in the usual fashion to the computer through the switch, while the IU is connected to the other input of the switch. When it is desired to input medical data the patient need only throw the switch to connect data through from the IU and to disconnect the other input.

Computer 212 is a typical conventional computer of any commercial make, and is also referred to simply as a PC. The computer comprises a microprocessor 213 and memory 215. The software loaded in memory provides numerous functions, but specifically for purposes of this application stores browser software downloaded for this application. The software contains an algorithm for storing the inputted medical data in a form suitable for transmission over the internet to the host computer. The computer system, or PC, typically includes an input device 218, which may be disc and/or CD, as well as a terminal 219, in the conventional manner.

Computer 212 has a standard Internet connection for connecting over the Internet to a host computer 220. In practice, when a patient logs on to a dedicated web site for delivery of the medical data, the host computer web site transfers plug in software back to the patient's computer, for storage in memory indicated by block 215. At the dedicated software web site the downloaded data can be stored and analyzed, and messages are generated and forwarded back to the patient computer as appropriate. Indeed, the system is bi-directional, since the reply message may be of several forms. The reply message may give written comment on the analysis of the data; or make written directions as to steps that should be taken by the patient such as medications to be taken. It may also contain control signals to be communicated back through the IU to the programmer for reprogramming one or more functions of the implanted device.

FIG. 4 also shows at 225 additional apparatus, or alternative apparatus for measuring various biological signals. Thus, one or more additional configurations may be connected through to port 210, preferably through switch 206. It is to be noted that in a preferred embodiment the keyboard port is used, enabling the patient to combine typed information with medical information. Thus, a patient typically can download a certain amount of signal data into the computer for transmission to the web site; and then add written comment giving additional patient information that can be useful for analysis at the web site. In this case the patient throws the switch 206 to connect the IU to provide signal data, and then changes switch 206 again to use the keyboard for interspersing comment which contains additional information.

Figures 5, 6:
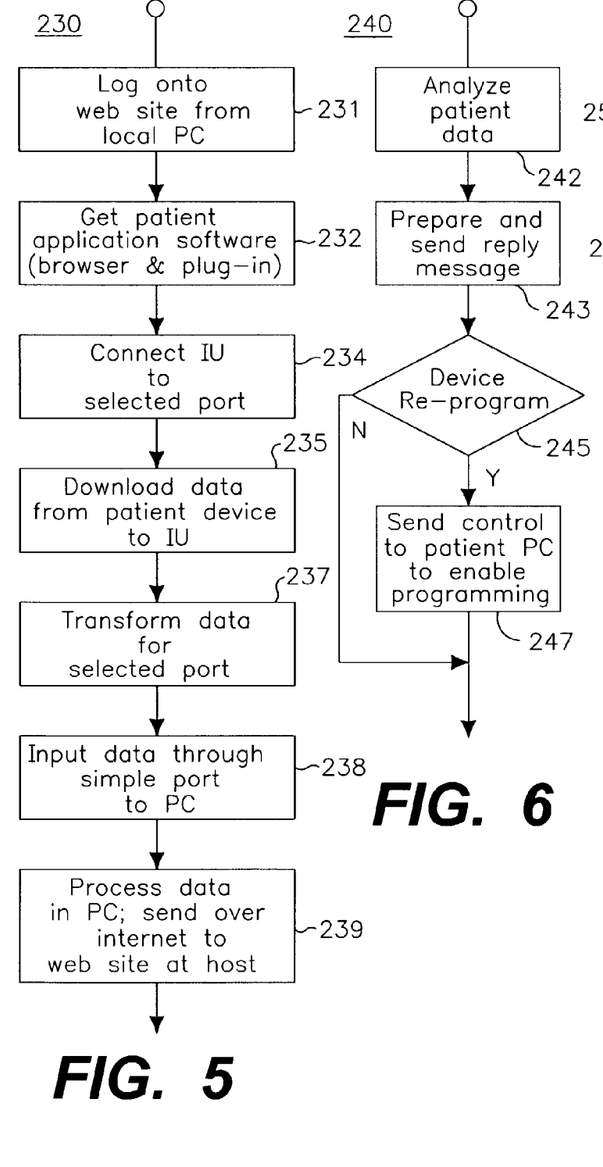
FIG. 5 is a flow diagram showing steps taken in the method of this invention in downloading patient data to a dedicated web site.
FIG. 6 is a flow diagram showing the operation at the host web site in analyzing data and sending a reply message back to the patient's computer.

FIGS. 5 through 8 are flow diagrams that illustrate the techniques of this invention, and the utilization of the system as discussed in connection with FIG. 4. FIG. 5 shows a routine 230 for downloading patient data. At 231, the patient logs on to the web site from his or her local personal computer (PC), for interconnection with a specific patient file. The patient's PC may of course be at the patient's home, or may be virtually anywhere that the patient is currently located or is visiting. The patient need only have a simple hand held programmer and the interface unit in order to log on to the computer. At 232, the patient computer receives application software from the web site in the form of browser and plug in data in response to the personalized log in by the patient. At 234, the patient connects the IU, preferably through a switch, to the selected simple port, either keyboard or mouse. Of course, it is to be understood that this connection may be made before or after logging onto the web site. At 235, the patient downloads data from the patient signal source, e.g. implanted pacemaker, to the IU. At 237, the IU transforms the data to the selected simple port, i.e., into the mouse or keyboard type data. At 238, the data is transmitted through the port to the PC, and at 239 the data is put into suitable form by the computer for sending over the internet to the web site located at the host. It is noted that the inputted "mouse" or "keyboard" data can be transformed back into signal data either at the patient's PC or at the web site computer.

FIG. 6 illustrates routine 240 which is carried out at the host, containing the dedicated web site. At 242, the patient data is received and analyzed by, e.g., a physician, artificial intelligence software or pacemaker expert. At 243, a reply message is prepared and sent back to the patient. This can be done automatically, based on data already in the patient file; or it can be done after review by a physician or other trained person located at the web site. Additionally, the host may determine whether control signals should be sent back to the patient for, e.g., reprogramming an implantable device. If, at 245, it is decided to reprogram the device, then at 247 one or more programmed control signals are forwarded back to the patient PC, enabling a the programmer for re-programming one or more operational features. Thus, for an implantable pacemaker, the decision may be to select a different pacing therapy program that is already stored in the programmer, change the pacing rate limits, etc.

Figure 7:
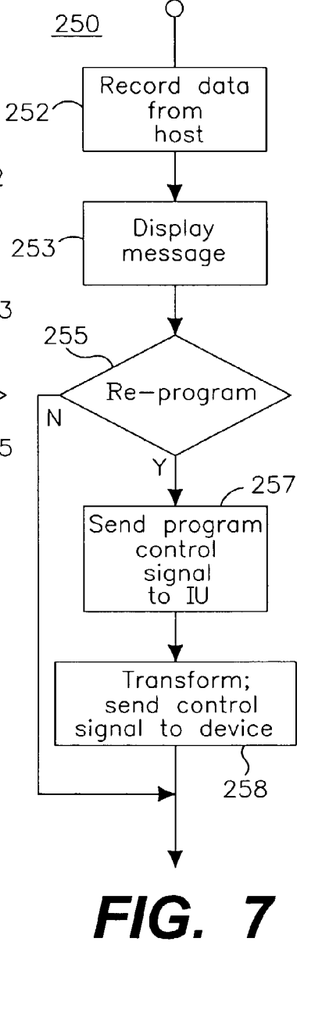
FIG. 7 is a flow diagram illustrating uploading data at the patient's computer that has been received from the host.

FIG. 7 illustrates a routine 250, that provides steps for uploading data at the patient's PC. At 252, the data and other messages are received from the host web site, and displayed at 253. At 255, it is determined whether a reprogram signal has been forwarded from the host. This is done, e.g., by reading a written instruction, or automatically by the computer. If there is a reprogram signal or instruction, at 257 a program control is generated, as by the patient entering a control command through the keyboard, and sent to the IU device. Alternately, the computer can send the control signal directly to the IU without patient intervention. At 258 the IU transforms the control signal appropriately and sends it to the control device.

Figure 8:
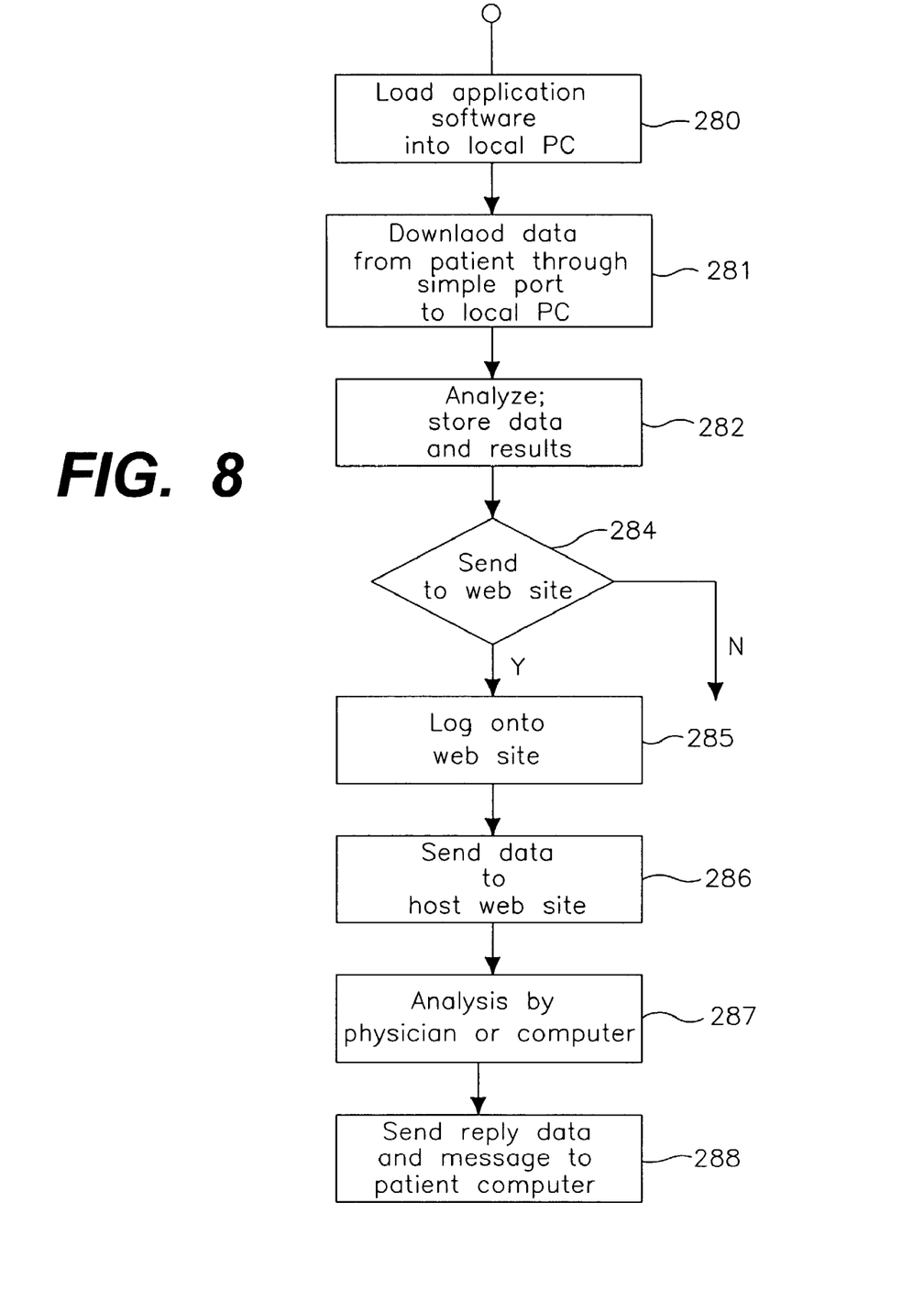
FIG. 8 is a flow diagram showing an alternate embodiment of method of this invention wherein the patient obtains data relatively frequently and downloads it into a computer, and periodically sends data to the dedicated web site for analysis.

FIG. 8 shows an alternate manner of utilizing the system and method of this invention. In the routine of FIG. 8, it is assumed that the patient is monitoring one or more medical conditions frequently, and periodically downloads data to the dedicated web site. For example, a patient with an implanted pacemaker or a diabetic may obtain signal data or other information daily but need only download the data to the web site on a weekly basis. In this situation, special application software can be loaded into the patient PC, as shown at 280. The special application software carries out the function of organizing the data that is inputted by the patient, and arranges it for subsequent use at the web site, e.g., arranges it in histogram form, or on a historical basis. As shown at 281, the patient periodically downloads data through the simple port to the local PC. At 282, this data is analyzed and stored. Each time this happens, at 284 a decision is made as to whether to send the data to the web site. As discussed above, this may involve simply determining whether a certain period of time has passed, or it may it involve determining how many data samples have been inputted. If it is not time to send data to the web site, the routine exits. However, if it is appropriate to send data to the web site, then at 285 the patient logs onto the web site, and at 286 the data is sent through to the host web site. The data is analyzed either by computer or by a physician or other trained person as indicated at 287 and at 288 reply data and/or a message is sent back to the patient. The patient then takes appropriate action.

FIG. 9 is a block diagram that shows the primary components of a combined programmer/interface unit 204, as well as a pacemaker device 10. The pacemaker has a microprocessor circuit 58 that interconnects with pacing circuitry 54, as also seen in FIG. 3. The pacing circuitry transmits pacing pulses to heart 8, and receives cardiac signals back from the heart. Stored data, or continuously received cardiac signals can be downloaded through coil 56 to coil 300 of the device 204, in a known manner; likewise, control signals can be transmitted from coil 300 back to the pacemaker. While a pacemaker is illustrated as a suitable device for use with this invention, other implantable devices can likewise be used.

Device 204 is preferably a hand-held battery-powered device that is portable and can be easily carried by the patient. As shown, a battery 325 provides power, which is switchable on and off by switch S in control console 316. Other controls, illustrated as provided by button activated switches, include, by way of example:

A. Get data from pacer, convert A to D, and store.
B. Transmit stored data to a computer.
C. Get data from pacer, convert and transmit directly to computer.
D. Send programming signal to pacer.
E. Enable auxiliary port.

It is to be noted that a more sophisticated device may incorporate a conventional programmer, to which has been added the interface capability of this invention. Such a combined programmer and IU may be used by a physician for inputting data and control instructions. However, such a relatively complex and expensive device is not intended for patient use. The invention provides a very simple device, with a simple console, providing portability and easy use by the patient. The patient device 204 may incorporate a simple keyboard console in place of buttons.

Data is received from the implanted device through antenna coil 300. The received signal is connected to telemetry/antenna driver circuit 302 that serves to demodulate telemetry signals received from antenna 56 of the pacemaker. The demodulated signals are applied in parallel or serial digital format to input/output (I/O) unit 308, where they in turn may be applied to a small display 310, and/or provided to central processing unit and memory 314. Unit 314 includes a microprocessor for controlling operation of the display apparatus, and is responsive to commands from console 316 (or from a keyboard). Unit 314 also contains suitable memory for storing data and for controlling the data transformation operations. The device has an output port shown at 318, for connection through a suitable cable 320 (FIG. 4) to the switch 206 or directly to the bi-directional computer simple port 210. FIG. 9 also illustrates an input port 328 for receiving signals from an auxiliary source, such as an EKG machine, blood analyzer, glucose monitor, etc. Signals from the auxiliary source can be processed in the same manner as described above for signals coming from an implanted pacemaker.

Figure 10:
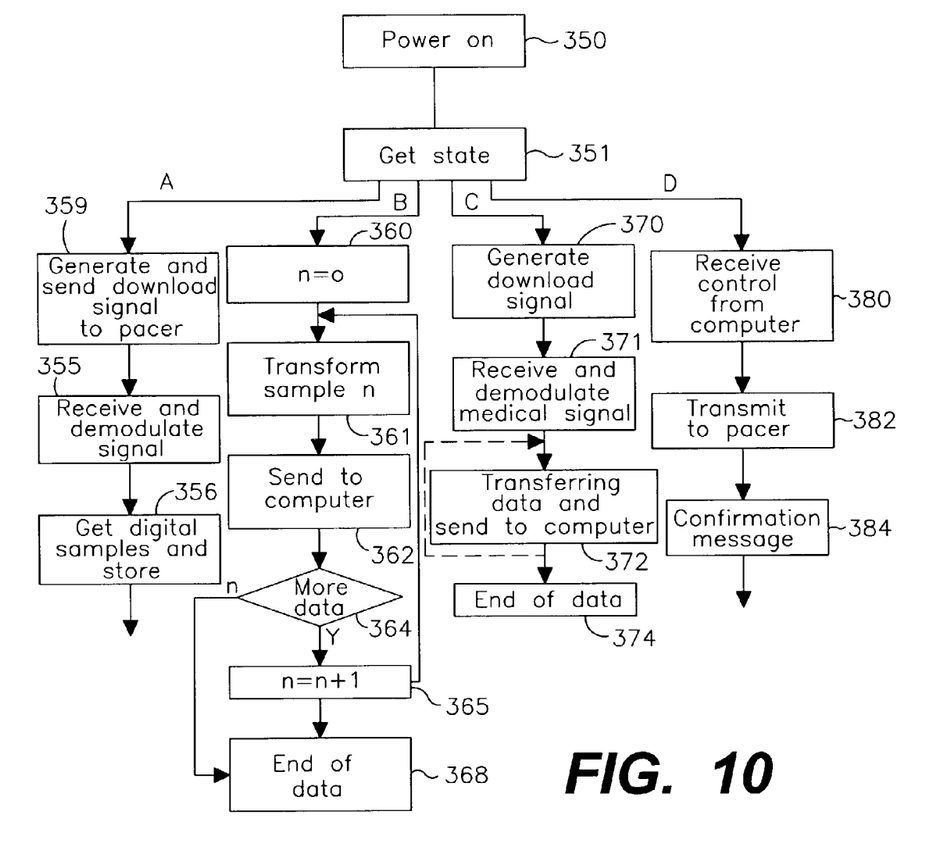
FIG. 10 is an overview flow diagram showing the operation of the device 204 illustrated in FIG. 9.

FIG. 10 is an overview flow diagram, showing operational steps taken by the device 204 of FIG. 9. At 350, power is turned on, by operation of switch S. At 351, the device recognizes when one of the state buttons has been pressed, i.e., state buttons A–D. If the device has been placed in state A, the routine goes to 354 and generates and sends a download signal to the pacemaker. Then, at 355 the telemetered signal is received and demodulated. At 356, A/D conversion is done for an analog signal, and the digital sample values are stored in device memory.

When in state B, with downloaded data already in device storage, the routine goes to 360 and sets a counter to zero (n=0). At 361, the routine takes the first digital value and transforms it for reception by the simple port of the computer. As discussed above, this is done by use of a lookup table for transforming each sample value into an appropriate mouse or keyboard signal. For example, each increment from one sample to the next is represented by an assigned keyboard character or combination of characters. Since the samples are separated by a constant time increment, a specific keyboard symbol such as a comma may be inserted to identify the respective data points. At 362, the transformed digital value is connected to the computer through the simple port. At 364, it is determined whether there is more signal data to be sent. If the answer is no, the routine branches to 368 and generates and sends to the computer an "end of data" symbol, in either keyboard or mouse format. However, as long as there is more data to be sent, the routine goes from 364 to 365 and increments n=n+1, and then loops back to transform the next digital sample.

If the device is in state C, the microprocessor routine goes to 370 and generates a download signal, and sends it to the implanted pacemaker or other signal source. AT 371, the signal is received, demodulated and converted to digital values. At 372, the routine carries out the transformation steps, looping through each transformation until all data has been transformed and sent to the computer in a serial fashion. Then, at 374, the end of data signal is sent to the PC.

Finally, for state D, at 380 the device receives a control signal from the computer. This is followed at 382 by transmitting the control signal to the implanted pacemaker for reprogramming the pacemakerAt 384 a confirmation message is presented on the computer screen, and transmitted to the host computer, to confirm that the pacemaker has been properly programmed.

The preceding specific embodiments are illustrative of the practice of the invention. It is to be understood, therefore, that other expedients known to those skilled in the art or disclosed herein, may be employed without departing from the invention or the scope of the appended claims. The present invention is not limited to any particular combination of hardware and software per se, but may find application with any form of software supplementing hardware. Further, the invention is not limited with respect to the activities carried out at the dedicated web site. Any computer that has a simple port, or has a port that has been modified to present a simple port, can be used in the practice of this invention.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A system for transmitting medical type data obtained from a person to a dedicated web site for analysis, comprising:
   a computer system accessible to said person, said computer system having at least one simple port for receiving data in a prescribed form;
   signal means for obtaining data from said person;
   transform means for transforming said data into said prescribed form;
   a circuit connection for connecting said transformed data to said simple port; and
   said computer system having web site means for connecting through the internet to a dedicated web site, wherein said computer system has a mouse and a mouse port, and said circuit connection comprises a switch for providing a switchable connection between said transform means and said mouse port.

2. The system as described in claim 1, wherein said computer system comprises a PC having a keyboard port, and said circuit connection connects said transformed data to said keyboard port.

3. The system as described in claim 1, wherein said computer system comprises a PC having a mouse port, and said circuit connection has means for connecting said transformed data to said mouse port.

4. The system as described in claim 1, wherein the person has an implanted medical device, said signal means comprises a pacemaker programmer for receiving cardiac signals from the implanted medical device, and said transform means comprises means for transforming said cardiac signals into data acceptable for said simple port.

5. The system as described in claim 1, wherein said person has an implanted medical device with means for receiving command signals, said computer system comprising a PC having a bi-directional simple port, said transform means comprising a bi-directional circuit, said circuit connection having means for providing bi-directional data transmission between said transform means and said port, said signal means having re-program means for transmitting a command signal to said implanted medical device, and wherein said computer system PC has loaded software for directing a command signal to be passed through said port for transmission to said implanted medical device.

6. The system as described in claim 1, wherein said signal means comprises an implanted device having a telemetry system for transmitting signals, and a programmer device having receiving means for receiving said transmitted signals.

7. A system for obtaining and transferring medical data from a patient into a focal computer having a simple port for receiving data of a predetermined form, comprising:
   means for obtaining medical data from a patient;
   interface means for transforming said data into said predetermined form; and
   a connection circuit for connecting said transformed data into said simple port, wherein said local computer has a mouse nod, said interface means comprises means for transforming said data into mouse data, and said connection circuit is connected between said interface means and said mouse port.

8. The system as described in claim 7, further comprising a dedicated web site at a remote computer, each of said local computer and said remote computer being connected to the internet, and said local computer having software for transmitting said transformed data over the internet to said remote computer and for receiving messages back from said remote computer.

9. A method of transmitting data between a source of patient data and a web site available on The internet, comprising:
   providing the patient with a patient computer that has at least one simple bi-directional port, and logging on from said patient computer to a dedicated web site;
   transforming said patient data to the prescribed form for said simple port; and
   connecting said transformed data to the computer through said simple port; and
   transmitting said data from said patient computer to said website over the internet, wherein said simple bi-directional part is a keyboard port, and further comprising:
   transforming said data in a portable interface unit, and switching said interface unit into connection with said keyboard port.

10. The method as described in claim 9, wherein said patient has an implanted medical device, and comprising:
    telemetering data from said implanted device and receiving said data in an external T/R device, connecting said data from said T/R device to said portable interface unit, and logging on to said web site from said patient computer.

11. The method as described in claim 10, comprising processing said data at said web site, and sending reply information to said patient computer from said web site.

12. The method as described in claim 11, comprising sending a command signal from said web site, and transmitting said command signal through said port, said interface device and said T/R device to said implanted medical device.

13. The method as described in claim 9, comprising alternately connecting transformed data and keyboard data through said port, and transmitting said transformed data and keyboard data to said web site.

14. The method as described in claim 9, comprising periodically transforming data from said source, connecting said transformed data to said computer, and storing said data; determining when to transmit said stored data to said web site; and transmitting said stored data to said web site upon determining to do so.

15. The method as described in claim 9, comprising positioning a medical device as a source for obtaining medical data from the patient, transferring said data to a portable interface unit, and transforming said data in said interface unit.

16. The method as described in claim 15, comprising obtaining cardiac signal data from an implanted pacemaker type device, telemetering said data to a pacemaker programmer type device, and connecting said telemetered data through said portable interface unit to said patient computer.

17. The method as described in claim 16, comprising analyzing the data that has been transmitted to said web site, and sending a reply message from said web site to said patient computer.

18. The method as described in claim 17, wherein said sending comprises sending an instruction for use in changing an operation of said implanted device.

19. The method as described in claim 9, wherein said patient computer has two of said simple ports, selecting one of said simple ports, and connecting said transformed data to said selected port.

20. The method as described in claim 15, comprising: providing an alternate data source that outputs data with said prescribed form, providing a switch with a plurality of inputs and at least one output, connecting said switch output to a selected computer port, and selectively switching one of said interface unit and said alternate data source to said switch output for connection to said computer.

21. The method as described in claim 20, wherein said computer has a keyboard port, and comprising providing a keyboard as said alternate data source.

22. A method of providing for transmission of medical data from a patient to an internet web site, said method being easily carried out wherever and whenever The patient has access to a computer having at least one simple port, comprising:
    using a signal source device for obtaining medical data from the patient;
    providing a portable data transforming device for transforming the obtained medical data into a prescribed form for entry into said simple port;
    providing a dedicated web site available over the internet;
    using said computer to log onto said web site;
    transferring medical data from said signal source to said portable data transforming device, and transforming said data in said portable device;
    connecting said transformed data through said simple port; and
sending said data over the internet to the dedicated web site; and
    receiving and analysing said data at said web site, and transmitting reply data to a said computer to which the patient has access.

23. The method as described in claim 22, wherein said patient has an implanted pacemaker type device, comprising collecting cardiac data with said pacemaker type device and downloading said data to a transmit/receive device, and transferring said data to said portable data transforming device.

24. The method as described in claim 22, comprising providing a signal pickup device and using said signal pickup device to obtain said patient medical data, and connecting said signal pickup device to said portable data transforming device.

25. The method as described in claim 22, wherein said computer has a keyboard port, and comprising connecting said transformed data to and through said keyboard port.

26. The method as described in claim 22, wherein said computer has a mouse port, and comprising connecting said transformed data to and through said mouse port.

27. The method as described in claim 22, comprising transmitting data from said patient computer to said web site a plurality of times, storing said transmissions of data, analyzing said data each time another transmission has been received at the web site, and sending a reply message as a function of said analyzing.

28. The method as described in claim 22 comprising using an EKG device to obtain a patient EKG, and transferring said patient EKG to said portable data transforming device.

29. The method as described in claim 22, comprising inputting keyboard data into said computer, and transmitting both said data and said keyboard data over the internet to said dedicated web site.

30. A portable battery powered device for transferring data between a patients implanted pacemaker and a computer, the computer having at least one simple port, the pacemaker having a telemetry system for sending signals containing encoded data to an external receiver, said portable device comprising:
    a receiver for receiving data signals from said pacemaker;
    decoding means for decoding data from said signals;
    transform means for transforming said data into a form adapted for entry through said simple port; and
    download means operable by a patient for transferring said transformed data to said port, said download means having an input/output port, whereby said data can be downloaded into a computer by said patient when said input/output port is connected to said computer simple port.

31. The device as described in claim 30, comprising initiate means for initiating transmission of data signals from said implanted pacemaker.

32. The device as described in claim 31, comprising selection means for selecting alternately storing said transformed data or downloading it to the computer.

33. The device as described in claim 31, comprising selection means for providing a plurality of options for receiving data and transmitting data.

34. The device as described in claim 33, comprising control means for enabling receipt of a control signal from said computer and for transmitting said control signal to the pacemaker.

35. The device as described in claim 31, comprising a plurality of input ports, and selection means for selecting one of said input ports for interconnection of said device to an external source of data.

36. The device as described in claim 31, wherein said transform means comprises algorithm means for carrying out said transforming.

37. The device as described in claim 36, wherein said algorithm means comprises keyboard means for transforming said data into a form adapted for entry through a computer keyboard port.

38. The device as described in claim 36, wherein said algorithm means comprises mouse means for transforming said data into a from adapted for entry through a computer mouse port.

* * * * *

UNITED STATES PATENT AND TRADEMARK OFFICE
CERTIFICATE OF CORRECTION

PATENT NO.         : 7,082,334 B2
APPLICATION NO.    : 10/020880
DATED              : July 25, 2006
INVENTOR(S)        : Willem Boute et al.

It is certified that error appears in the above-identified patent and that said Letters Patent is hereby corrected as shown below:

Col. 12, line 16, delete "mouse nod" and insert --mouse port--.

Col. 12, lines 38 and 39, delete "bi-directional part" and insert --bi-directional port--.

Col. 14, line 11, delete "In claim 22" and insert --in claim 22,--.

Col. 14, line 19, delete "a patients" and insert --a patient's--.

Signed and Sealed this

Second Day of January, 2007

JON W. DUDAS
*Director of the United States Patent and Trademark Office*